US012751975B2

(12) United States Patent
Ishidome et al.

(10) Patent No.: US 12,751,975 B2
(45) Date of Patent: Oct. 6, 2026

(54) ANTI-INFLAMMATORY AGENT AND METHOD OF PRODUCING EXTRACELLULAR VESICLE HAVING ANTI-INFLAMMATORY ACTION

(71) Applicant: FUJIFILM Wako Pure Chemical Corporation, Osaka (JP)

(72) Inventors: Takamasa Ishidome, Amagasaki (JP); Masayuki Yamane, Amagasaki (JP)

(73) Assignee: FUJIFILM WAKO PURE CHEMICAL CORPORATION, Osaka (JP)

( * ) Notice: Subject to any disclaimer, the term of this patent is extended or adjusted under 35 U.S.C. 154(b) by 977 days.

(21) Appl. No.: 17/866,167

(22) Filed: Jul. 15, 2022

(65) Prior Publication Data

US 2023/0126684 A1 Apr. 27, 2023

Related U.S. Application Data

(63) Continuation of application No. PCT/JP2021/001130, filed on Jan. 14, 2021.

(30) Foreign Application Priority Data

Jan. 15, 2020 (JP) ................................ 2020-004766

(51) Int. Cl.
*A61K 35/28* (2015.01)
*A61P 29/00* (2006.01)

(52) U.S. Cl.
CPC .............. *A61K 35/28* (2013.01); *A61P 29/00* (2018.01)

(58) Field of Classification Search
CPC ................................ A61K 35/28; A61P 29/00
See application file for complete search history.

(56) References Cited

U.S. PATENT DOCUMENTS

| | | | |
|---|---|---|---|
| 5,200,471 A | 4/1993 | Coleman et al. | |
| 2013/0197206 A1 | 8/2013 | Nishibu et al. | |
| 2018/0120299 A1 | 5/2018 | Nishibu et al. | |
| 2018/0371418 A1* | 12/2018 | Yang ..................... | A61K 35/28 |

FOREIGN PATENT DOCUMENTS

| | | |
|---|---|---|
| JP | 5-41946 A | 2/1993 |
| JP | 3269554 B2 | 3/2002 |
| KR | 10-2047768 B1 | 11/2019 |
| WO | WO 2012/039395 A1 | 3/2012 |
| WO | WO 2016/088689 A1 | 6/2016 |
| WO | WO 2018/182356 A1 | 10/2018 |

OTHER PUBLICATIONS

Hu et al. (Exosomes secreted by Human-Induced pluripotent Stem cell-Derived mesenchymal stem Cells attenuate limb ischemia by promoting angiogenesis in mice), Stem Cell Research & Therapy 2015, 6:10.*

Japanese Office Action for corresponding Japanese Application No. 2021-571237, dated May 23, 2023, with English translation.

Extended European Search Report for corresponding European Application No. 21741243.6, dated Jun. 26, 2023.

Kobayashi et al., "Effects of exosomes derived from the induced pluripotent stem cells on skin wound healing," Nagoya J. Med. Sci., vol. 80, 2018, pp. 141-153.

Liu et al., "Exosomes from adipose-derived mesenchymal stem cells prevent cardiomyocyte apoptosis induced by oxidative stress," Cell Death Discovery, vol. 5, No. 79, 2019, pp. 1-7.

Japanese Office Action dated Nov. 21, 2023 for corresponding Application No. 2021-571237 with an English translation.

Aoki, "Adiposomes: functional membrane vesicles secreted by adipocytes," Obesity Research, vol. 13, No. 2, 2007, pp. 209-211 (6 pages total), with English translation.

Cao et al., "Extracellular vesicles derived from bone marrow mesenchymal stem cells attenuate dextran sodium sulfate-induced ulcerative colitis by promoting M2 macrophage polarization," International Immunopharmacology, vol. 72, 2019 (Available online Apr. 17, 2019) pp. 264-274.

International Preliminary Report on Patentability and English translation of the Written Opinion of the International Searching Authority (Forms PCT/IB/326, PCT/IB/373 and PCT/ISA/237) for International Application No. PCT/JP2021/001130, dated Jul. 28, 2022.

International Search Report (Form PCT/ISA/210) for International Application No. PCT/JP2021/001130, dated Mar. 9, 2021, with English translation.

Lo Sicco et al., "Mesenchymal Stem Cell-Derived Extracellular Vesicles as Mediators of Anti-Inflammatory Effects: Endorsement of Macrophage Polarization," Stem Cells Translational Medicine, vol. 6, 2017, pp. 1018-1028.

Mathieu et al., "Specificities of secretion and uptake of exosomes and other extracellular vesicles for cell-to-cell communication," Nature Cell Biology, vol. 21, Jan. 2019, pp. 9-17.

Thery et al., "Membrane vesicles as conveyors of immune responses," Nature Reviews Immunology, vol. 9, Aug. 2009, pp. 581-593.

Zhou et al., "Bone marrow mesenchymal stem cell-derived exosomes reduce the activation of type A1 astrocytes after spinal cord injury," Chinese Journal of Tissue Engineering Research, 2019, pp. 3294-3301, with English Abstract.

European Communication pursuant to Article 94(3) EPC for corresponding European Application No. 21 741 243.6, dated Oct. 21, 2025.

Chinese Office Action and Search Report for Chinese Application No. 202180009496.7, dated Jun. 27, 2026.

* cited by examiner

*Primary Examiner* — Zohreh A Fay
(74) *Attorney, Agent, or Firm* — Birch, Stewart, Kolasch & Birch, LLP

(57) ABSTRACT

The present invention relates to an anti-inflammatory agent comprising an extracellular vesicle that is obtained by a method of using a substance having an affinity for phosphatidylserine obtained from a mesenchymal stem cell-derived extracellular vesicle, as an active ingredient, and a method of producing an extracellular vesicle having an anti-inflammatory action, the method including a step of obtaining an extracellular vesicle from a mesenchymal stem cell-derived extracellular vesicle by a method in which a substance having an affinity for phosphatidylserine is used.

4 Claims, 8 Drawing Sheets

Specification includes a Sequence Listing.

| | Forward | Reverse |
|---|---|---|
| TNF$\alpha$ | CTGGTATGAGCCCATCTATCTG (SEQUENCE NUMBER 1) | CAATGATCCCAAAGTAGACCTG (SEQUENCE NUMBER 2) |
| IL-6 | ACAGACAGCCACTCACCTCT (SEQUENCE NUMBER 3) | CAGTGCCTCTTTGCTGCTTT (SEQUENCE NUMBER 4) |
| TGF$\beta$1 | CAACTATTGCTTCAGCTCCACG (SEQUENCE NUMBER 5) | GTGTCCAGGCTCCAAATGTAG (SEQUENCE NUMBER 6) |

```
                         SEQUENCE LISTING

Sequence total quantity: 6
SEQ ID NO: 1             moltype = DNA  length = 22
FEATURE                  Location/Qualifiers
misc_feature             1..22
                         note = oligonucleotide primer
source                   1..22
                         mol_type = other DNA
                         organism = synthetic construct
SEQUENCE: 1
ctggtatgag cccatctatc tg                                           22

SEQ ID NO: 2             moltype = DNA  length = 22
FEATURE                  Location/Qualifiers
misc_feature             1..22
                         note = oligonucleotide primer
source                   1..22
                         mol_type = other DNA
                         organism = synthetic construct
SEQUENCE: 2
caatgatccc aaagtagacc tg                                           22

SEQ ID NO: 3             moltype = DNA  length = 20
FEATURE                  Location/Qualifiers
misc_feature             1..20
                         note = oligonucleotide primer
source                   1..20
                         mol_type = other DNA
                         organism = synthetic construct
SEQUENCE: 3
acagacagcc actcacctct                                              20

SEQ ID NO: 4             moltype = DNA  length = 20
FEATURE                  Location/Qualifiers
misc_feature             1..20
                         note = oligonucleotide primer
source                   1..20
                         mol_type = other DNA
                         organism = synthetic construct
SEQUENCE: 4
cagtgcctct ttgctgcttt                                              20

SEQ ID NO: 5             moltype = DNA  length = 22
FEATURE                  Location/Qualifiers
misc_feature             1..22
                         note = oligonucleotide primer
source                   1..22
                         mol_type = other DNA
                         organism = synthetic construct
SEQUENCE: 5
caactattgc ttcagctcca cg                                           22
```

-continued

```
SEQ ID NO: 6            moltype = DNA  length = 21
FEATURE                 Location/Qualifiers
misc_feature            1..21
                        note = oligonucleotide primer
source                  1..21
                        mol_type = other DNA
                        organism = synthetic construct
SEQUENCE: 6
gtgtccaggc tccaaatgta g                                              21
```

ANTI-INFLAMMATORY AGENT AND METHOD OF PRODUCING EXTRACELLULAR VESICLE HAVING ANTI-INFLAMMATORY ACTION

CROSS-REFERENCE TO RELATED APPLICATIONS

This application is a Continuation of PCT International Application No. PCT/JP2021/001130 filed on Jan. 14, 2021, which claims priority under 35 U.S.C § 119(a) to Japanese Patent Application No. 2020-004766 filed on Jan. 15, 2020. Each of the above application(s) is hereby expressly incorporated by reference, in its entirety, into the present application.

REFERENCE TO SEQUENCE LISTING SUBMITTED VIA EFS-WEB

The application contains a Sequence Listing which has been submitted electronically in .XML format and is hereby incorporated by reference in its entirety. Said .XML copy, created on Jul. 14, 2022, is named "2022-07-15_Sequence-_Listing 2870-0815PUS1.xml" and is 8,493 bytes in size. The sequence listing contained in this .XML file is part of the specification and is hereby incorporated by reference herein in its entirety.

BACKGROUND OF THE INVENTION

1. Field of the Invention

The present invention relates to an anti-inflammatory agent composed of mesenchymal stem cell-derived extracellular vesicles.

2. Description of the Related Art

It is considered that extracellular vesicles that are derived from cells and are small membrane vesicles composed of lipid bilayers are responsible for intercellular communication through the transfer of nucleic acids such as mRNA and microRNA contained, or proteins (Mathieu M, Martin-Jaular L, Lavieu G, Thery C (2019) Specificities of secretion and uptake of exosomes and other extracellular vesicles for cell-to-cell communication. Nat Cell Biol, 21(1): 9-17).

Mesenchymal stem cells (hereinafter may be abbreviated as "MSCs") are somatic stem cells derived from mesoderm tissue. MSCs can be separated from adipose, bone marrow, umbilical cord matrix, or the like, all of which are believed to have in common the ability to adhesiveness, CD105, CD73, CD90 positive, CD45, CD34, CD14, CD11b, CD79a, CD19, HLA-Class II (DR)negative, differentiation potential into bone, adipose, and cartilage.

In recent years, it has been suggested that extracellular vesicles may be involved in various diseases. In addition, it has been reported that extracellular vesicles acquired from mesenchymal stem cell-derived extracellular vesicles by an ultracentrifugal method have an anti-inflammatory action (anti-inflammatory effect) (SC Lo et al. (2017) Mesenchymal Stem Cell-Derived Extracellular Vesicles as Mediators of Anti-Inflammatory Effects: Endorsement of Macrophage Polarization. Stem Cells Transl Med, 6 (3): 1018-1028).

SUMMARY OF THE INVENTION

The present inventors have examined the anti-inflammatory action of extracellular vesicles acquired from mesenchymal stem cell-derived extracellular vesicles by the ultracentrifugal method, and have found that the action was weak and insufficient for industrial use. In view of the above circumstance, an object of the present invention is to provide a therapeutic preparation composed of a population of extracellular vesicles having a higher therapeutic effect, particularly an anti-inflammatory agent.

In order to solve the above problems, the present inventors have diligently studied extracellular vesicles selectively recovered by various methods of acquiring extracellular vesicles. As a result, the present inventors have found that a population of extracellular vesicles having a feature such as PS positivity, which is acquired by a method of using a substance having an affinity for phosphatidylserine (PS) (PS-affinity method), is highly effective as an anti-inflammatory agent, and have completed the present invention.

That is, a basic aspect of the present invention includes:

(1) an anti-inflammatory agent comprising an extracellular vesicle that is obtained by a method of using a substance having an affinity for phosphatidylserine obtained from a mesenchymal stem cell-derived extracellular vesicle is used, as an active ingredient;

(2) the anti-inflammatory agent according to (1), in which the mesenchymal stem cell is derived from an iPS cell or a cell derived from one or more tissues selected from the group consisting of umbilical cord, umbilical cord blood, bone marrow, adipose, muscle, nerve, skin, amniotic membrane, and placenta;

(3) the anti-inflammatory agent according to (1) or (2), in which the substance having an affinity for phosphatidylserine is a Tim protein;

(4) the anti-inflammatory agent according to (3), in which the Tim protein is selected from Tim4 protein, Tim3 protein, and Tim1 protein.

The present invention is also to provide a method of producing such an anti-inflammatory agent, and specifically to provide (5) a method of producing an extracellular vesicle having an anti-inflammatory action, the method comprising: a step of obtaining an extracellular vesicle from a mesenchymal stem cell-derived extracellular vesicle by a method of using a substance having an affinity for phosphatidylserine;

(6) the method of producing an extracellular vesicle according to (5), in which the substance having an affinity for phosphatidylserine is a Tim protein;

(7) the method of producing an extracellular vesicle according to (6), in which the Tim protein is selected from Tim4 protein, Tim3 protein, and Tim1 protein.

The present invention is to provide the anti-inflammatory agent containing an extracellular vesicle that has an anti-inflammatory action and that is obtained from a mesenchymal stem cell, as an active ingredient. The anti-inflammatory agent provided in the present invention suppresses, for example, excessive production of inflammatory cytokines such as tumor necrosis factor (TNF-$\alpha$) and interleukin-6 (IL-6), or decreased production of anti-inflammatory cytokines such as TGF$\beta$1. Therefore, the anti-inflammatory agent can be an effective therapeutic medication for chronic inflammation such as rheumatoid arthritis and ulcerative colitis caused by a change in the production amount of these cytokines, crohn's disease, and furthermore, various diseases such as type 2 diabetes, depression, obesity, septicemia, atherosclerosis, dermatitis, dementia, general dementia, parkinson's disease.

DESCRIPTION OF THE PREFERRED EMBODIMENTS

Figure 1:
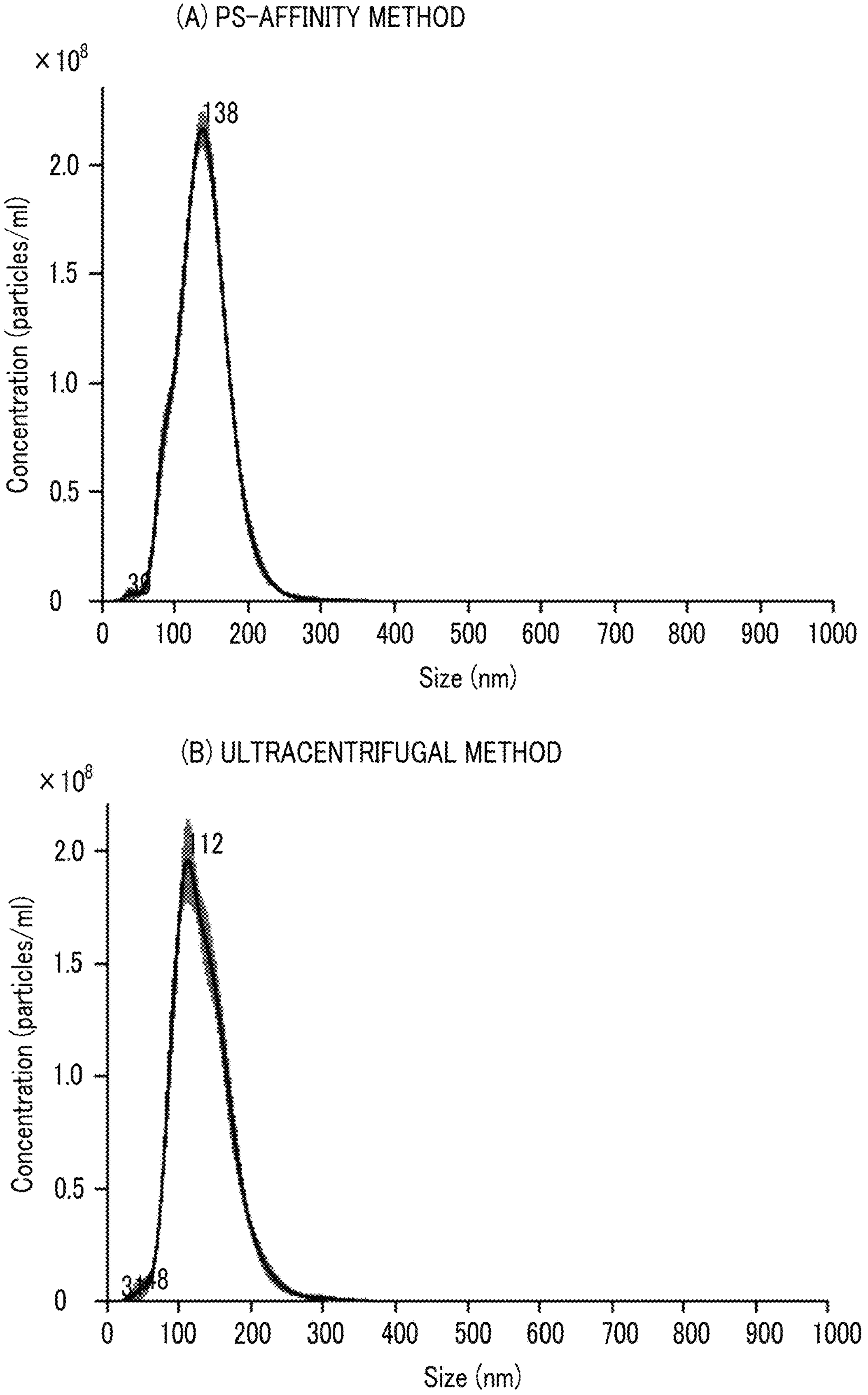
FIG. 1 is a diagram illustrating a result of analysis of a particle size distribution of MSC-derived extracellular vesicles acquired by a PS-affinity method and an ultracentrifugal method (ultracentrifugation method) by a nanoparticle tracking analysis (NTA) method.

As described above, a basic aspect of the present invention includes an anti-inflammatory agent containing an extracellular vesicle that is obtained by a method of using a substance having an affinity for phosphatidylserine obtained from a mesenchymal stem cell-derived extracellular vesicle, as an active ingredient.

An extracellular vesicle (hereinafter, may be abbreviated as "EV") is a small membrane vesicle derived from a cell and composed of a lipid bilayer. The extracellular vesicle usually has a diameter of 20 nm to 1000 nm, preferably 50 nm to 800 nm, more preferably 50 nm to 500 nm, and particularly preferably 50 nm to 200 nm. Examples of the extracellular vesicle include extracellular vesicles included in various classifications according to the origin of their occurrence, the size of small membrane vesicles, and the like as described in Nature Reviews Immunology 9,581-593 (August 2009), "Obesity Research" Vol. 13, No. 2, 2007, Topics Naoto Aoki and others. Specific examples thereof include exosomes, microvesicles, ectosomes, membrane particles, exosome-like vesicles, apoptotic vesicles, adiposomes, and the like, exosomes and microvesicles are preferable, and exosomes are more preferable.

The exosomes are cell-derived small membrane vesicles composed of lipid bilayers, and for example, each exosome has a diameter of 50 nm to 200 nm, preferably has a diameter of 50 nm to 150 nm, and more preferably has a diameter of 50 nm to 100 nm. The exosomes are believed to be derived from late endosomes.

The microvesicles are cell-derived small membrane vesicles composed of lipid bilayers, and for example, each microvesicle has a diameter of 100 nm to 1000 nm, preferably has a diameter of 100 nm to 800 nm, and more preferably has a diameter of 100 nm to 500 nm. The microvesicles are believed to be derived from cell membranes.

The MSCs are stem cells having differentiation potential into cells belonging to (mesenchymal) tissues derived from mesoderm such as osteoblasts, adipocytes, muscle cells, and chondrocytes. The MSCs can be separated from adipose, bone marrow, umbilical cord matrix, or the like, and the MSCs used in the present invention (hereinafter, may be abbreviated as "the MSCs according to the present invention") can be obtained by, for example, a method of separating MSCs from tissues derived from mesoderm or a method of inducing MSCs from stem cells such as iPS cells and ES cells. As the MSCs according to the present invention, cells derived from one or more tissues selected from the group consisting of umbilical cord, umbilical cord blood, bone marrow, adipose, muscle, nerve, skin, amniotic membrane, and placenta or cells derived from iPS cells are preferably used. Pretreatments such as recovery, concentration, purification, isolation, dilution with a buffer solution, and filtration sterilization may be performed on the MSCs according to the present invention. These pretreatments may be appropriately performed according to conventional methods in this field.

The extracellular vesicles as an active ingredient in an anti-inflammatory agent provided in the present invention are extracellular vesicles acquired by isolation from MSC-derived extracellular vesicles according to the present invention using a substance having an affinity for phosphatidylserine (hereinafter, may be abbreviated as "PS-positive extracellular vesicles"). The PS-positive extracellular vesicles are PS-positive (PS-containing) extracellular vesicles in which phosphatidylserine on a membrane surface of an extracellular vesicle is considered to be exposed.

As the substance having an affinity for phosphatidylserine (hereinafter, may be abbreviated as a "PS-affinity substance"), any substance may be employed as long as it can be specifically bonded to phosphatidylserine composing a membrane of an extracellular vesicle. Examples thereof include Annexin V; MFG-E8; Tim proteins such as Tim1 (T cell immunoglobulin mucin domain-containing molecule 1, T-cell immunoglobulin-mucin-domain 1) protein, Tim2 (T cell immunoglobulin mucin domain-containing molecule 2, T-cell immunoglobulin-mucin-domain 2) protein, Tim3 (T cell immunoglobulin mucin domain-containing molecule 3, T-cell immunoglobulin-mucin-domain 3) protein, and Tim4 (T cell immunoglobulin mucin domain-containing molecule 4, T-cell immunoglobulin-mucin-domain 4) protein, and from the viewpoint that extracellular vesicles can be efficiently acquired, Tim proteins are preferable, it is more preferable to be selected from Tim4 protein, Tim3 protein, and Tim1 protein, Tim4 protein and Tim1 protein are still more preferable, and Tim4 protein is particularly preferable.

The PS-positive extracellular vesicles are obtained by isolation from a cell culture supernatant liquid of the MSCs according to the present invention, which contains EV (hereinafter, may be abbreviated as a "cell culture supernatant liquid containing EV") using a substance having an affinity for phosphatidylserine, or by acquiring EV from a cell culture supernatant liquid of the MSCs according to the present invention, which contains EV, by a conventional method such as an ultracentrifugal method in this field, and isolating the PS-positive extracellular vesicles using a substance having an affinity for phosphatidylserine from the obtained EV. Among these, it is preferable to directly isolate extracellular vesicles from the cell culture supernatant liquid of the MSCs according to the present invention, which contains EV, using a substance having an affinity for phosphatidylserine. The MSCs according to the present invention are proliferated by cell culture, and the proliferated cells are further cultured in an EV production culture medium to obtain the cell culture supernatant liquid containing EV. The MSC cell culture according to the present invention and the culture in the EV production culture medium may be carried out according to a conventional method in this field, and the culture medium and culture conditions used are not particularly limited.

The outline of a method of acquiring extracellular vesicles by the method in which a substance having an affinity for phosphatidylserine (hereinafter, may be abbreviated as a "PS-affinity method") is used is described below. As the PS-affinity method, for example, a specific example is described in WO2016/088689A.

The PS-affinity method including brining the cell culture supernatant liquid containing EV into contact with a PS-affinity substance in the presence of calcium ions, forming a composite body (hereinafter, may be abbreviated as the "composite body according to the present invention") by combining the extracellular vesicles in the cell culture supernatant liquid with the PS-affinity substance, and separating the PS-affinity substance from the composite body to acquire PS-positive extracellular vesicles.

Specifically, a preferable method as the PS-affinity method includes following steps:

(1) a step of brining the cell culture supernatant liquid containing EV into contact with a PS-affinity substance in the presence of calcium ions, forming a composite body (the composite body according to the present invention) by combining the PS-positive extracellular vesicles in the cell culture supernatant liquid with the PS-affinity substance (hereinafter, may be abbreviated as the "composite body formation step");

(2) a step of separating the composite body according to the present invention obtained in the composite body formation step from the cell culture supernatant liquid containing EV (hereinafter, may be abbreviated as the "composite body separation step");

(3) a step of acquiring PS-positive extracellular vesicles by separation of the PS-positive extracellular vesicles from the composite body according to the present invention (hereinafter, may be abbreviated as the "acquisition step").

The cell culture supernatant liquid containing EV and the PS-affinity substance in the PS-affinity method are the same as those described above, and preferred and specific examples are also the same.

The PS-affinity substance used in the composite body formation step is preferably a substance immobilized (bonded) to an insoluble carrier. In this case, the composite body according to the present invention can be separated from the cell culture supernatant liquid containing EV by a known B/F separation method in the composite body separation step.

An example of a method of immobilizing a PS-affinity substance on an insoluble carrier will be described below, and a composite body can be obtained by, for example, a method described in WO2016/088689A.

Examples of the insoluble carrier for immobilizing the PS-affinity substance include an insoluble carrier used in an immunoassay method. Specific examples thereof include organic substances such as polystyrene, polyacrylic acid, polymethacrylic acid, polymethyl methacrylate, poly acrylamide, polyglycidylmethacrylate, polypropylene, polyolefin, polyimide, polyurethane, polyester, polyvinyl chloride, polyethylene, poly chlorocarbonate, a silicone resin, silicone rubber, agarose, dextran, and ethylene-maleic anhydride copolymer; inorganic substances such as glass, silicon oxide, silicon, porous glass, ground glass, alumina, silica gel, and metal oxides; magnetic materials such as iron, cobalt, nickel, magnetite, and chromite; and substances prepared from alloys of these magnetic materials. Examples of the usage form of these carriers include particles (beads), microplates, tubes, disc-shaped pieces, and the like. The form of the insoluble carriers is preferably particles (beads), and the size of each of the particles is not particularly limited, but for example, those have a size of 10 nm to 100 μm, and those preferably have a size of 100 nm to 10 μm.

Examples of a method of bonding the PS-affinity substance to the insoluble carrier include a method known per se for bonding a protein to a carrier. Examples of the method include a bonding method by affinity bonding, a bonding method by chemical bonding (for example, methods described in JP3269554B, WO2012/039395A), a bonding method by physical adsorption (for example, a method described in JP1993-41946B (JP-H05-41946)), or the like, the bonding method by physical adsorption and the bonding method by affinity bonding are preferable, and from the viewpoint of facilitation, the bonding method by physical adsorption is more preferable.

As a method of bonding the PS-affinity substance to the insoluble carrier by physical adsorption, the PS-affinity substance and the insoluble carrier are brought into contact with each other under a condition in which the PS-affinity substance and the insoluble carrier are bound, according to a method known per se.

The amount of the PS-affinity substance to be bonded to the insoluble carrier may be, for example, 0.1 μg to 50 μg, is preferably 0.1 μg to 30 μg, and is more preferably 0.1 μg to 20 μg, with respect to 1 mg of the insoluble carrier in a case where the insoluble carrier is the form of particles (beads), for example.

The physical adsorption of the PS-affinity substance and the insoluble carrier may be carried out, for example, by bringing a solution containing the PS-affinity substance into contact with the insoluble carrier.

In the solution containing the PS-affinity substance, a solution for dissolving the PS-affinity substance may be any solution as long as being capable of dissolving the PS-affinity substance in a stable state, and examples thereof include purified water, a buffer solution having a buffering action at pH 6.0 to 9.8, preferably 7.0 to 9.6 (for example, a Good's buffer solution, such as MOPS, or the like, a carbonate buffer solution, PBS, TBS, TBS-T, HBS or the like). The buffer agent concentration in these buffer solutions may be appropriately selected from a range of usually 5 to 100 mM, and preferably 10 to 100 mM. In a case where NaCl is added, the NaCl concentration is, for example, 100 to 200 mM, and is preferably 140 to 160 mM. Saccharides, salts such as NaCl, surfactants such as Tween (trademark) 20, preservatives, proteins, or the like may be contained in the solution containing the PS-affinity substance, as long as an amount thereof does not inhibit the bonding of the PS-affinity substance and the insoluble carrier.

Specific examples of the method of bonding the PS-affinity substance to the insoluble carrier by physical adsorption include the following methods. For example, 1 mg of a bead (particle) carrier and the solution containing the PS-affinity substance of 0.1 μg to 50 μg, preferably 0.1 μg to 30 μg, more preferably 0.1 μg to 20 μg are brought into contact with each other, and reacted with each other at 2° C. to 37° C., preferably 4° C. to 11° C. for 0.5 to 48 hours, preferably 0.5 to 24 hours.

The insoluble carrier to which the PS-affinity substance obtained as described above is immobilized may be subjected to a blocking treatment usually performed in this field.

The composite body formation step is carried out in the presence of calcium ions. Calcium ions are present in a case where the PS-affinity substance is brought into contact with the PS-positive extracellular vesicles in the cell culture supernatant liquid containing EV. The concentration of calcium ions in a case where the PS-affinity substance is brought into contact with the PS-positive extracellular vesicles in the cell culture supernatant liquid containing EV is usually 0.5 mM to 100 mM, preferably 1.0 mM to 10 mM, and more preferably 2.0 mM to 5.0 mM. The above described concentration of calcium ions is required in the solution containing the composite body according to the present invention until the composite body according to the present invention is formed by bringing the PS-affinity substance into contact with the PS-positive extracellular vesicles in the cell culture supernatant liquid containing EV and the composite body separation step is carried out, that is, until the step of separating the composite body according to the present invention is carried out.

What the calcium ions are derived from is not particularly limited, and examples thereof include calcium chloride, calcium hydroxide, calcium hydrogencarbonate, calcium iodide, calcium bromide, and calcium acetate, calcium chloride, calcium hydrogencarbonate, and calcium iodide are preferable, and calcium chloride and calcium hydrogencarbonate are more preferable.

As a method of allowing calcium ions to be present in a case where the PS-affinity substance is brought into contact with the PS-positive extracellular vesicles in the cell culture supernatant liquid containing EV, the calcium ion as described above may be contained in the cell culture supernatant liquid containing EV or/and the solution containing the PS-affinity substance so that the concentration of calcium ions in a case where the PS-affinity substance is brought into contact with the PS-positive extracellular vesicles in the cell culture supernatant liquid containing EV is in the above described range. In addition, a solution containing the amount of calcium ions in which the concentration of calcium ions in a case where the PS-affinity substance is brought into contact with the PS-positive extracellular vesicles in the cell culture supernatant liquid containing EV is in the above described range (hereinafter, may be abbreviated as the "calcium ion-containing solution"), the cell culture supernatant liquid containing EV, and the solution containing the PS-affinity substance may be mixed with each other.

In the calcium ion-containing solution according to the present invention, a solution for dissolving calcium ions may be any solution that does not inhibit bonding of the PS-positive extracellular vesicles and the PS-affinity substance, and examples thereof include water and a buffer solution having a buffering action at pH 7.0 to pH 8.0, and a buffer solution having a buffering action at pH 7.2 to pH 7.6 (for example, TBS, HBS, or the like) is preferable. A phosphate buffer is not preferable since the phosphate buffer and calcium are bonded to cause precipitation. The buffer agent concentration in these buffer solutions is appropriately selected from a range of usually 5 mM to 50 mM, and preferably 10 mM to 30 mM. In a case where NaCl is added, the NaCl concentration is usually selected from the range of 100 mM to 200 mM, and appropriately selected from the range of 140 mM to 160 mM.

For example, saccharides, salts such as NaCl, surfactants, preservatives, proteins such as BSA, or the like may be contained in the calcium ion-containing solution according to the present invention as long as an amount thereof does not inhibit the bonding of the PS-positive extracellular vesicles and the PS-affinity substance. Examples of the surfactants include Tween (trademark) 20 and the like, and the concentration of a surfactant in the calcium ion-containing solution according to the present invention is usually 0.00001% to 0.2%, and preferably usually 0.0005% to 0.1%.

In the composite body formation step, the amount of the cell culture supernatant liquid containing EV to be brought into contact with 1 μg of the PS-affinity substance (that may be immobilized on the insoluble carrier) is usually 0.1 ml to 100 ml, preferably 0.1 ml to 10 ml, and more preferably 0.1 ml to 1.0 ml. The temperature at which the cell culture supernatant liquid containing EV is brought into contact with the PS-affinity substance is usually 2° C. to 37° C., preferably 4° C. to 37° C., and more preferably 4° C. to 30° C. The time when the cell culture supernatant liquid containing EV is being brought into contact with the PS-affinity substance is usually 0.5 to 24 hours, preferably 0.5 to 8 hours, and more preferably 0.5 to 4 hours.

In a case where the insoluble carrier on which the PS-affinity substance is immobilized is used in the composite body formation step, the amount of the carriers is usually 0.1 mg to 20 mg per 1 mL of a solution for forming the composite body according to the present invention, preferably 0.3 mg to 10 mg, and more preferably 0.5 mg to 6.0 mg.

The composite body formation step may be performed by, for example, the following method. That is, the insoluble carriers on which the PS-affinity substance is immobilized in an amount of usually 0.1 mg to 20 mg, preferably 0.3 mg to 10 mg, and more preferably 0.5 mg to 6.0 mg per 1 mL of a solution after the cell culture supernatant liquid containing EV, the insoluble carriers on which the PS-affinity substance is immobilized, and the calcium ion-containing solution according to the present invention are mixed with each other, the calcium ion-containing solution according to the present invention in an amount such that the calcium ion concentration in a solution after the cell culture supernatant liquid containing EV, the carriers, and the calcium ion-containing solution are mixed with each other is usually 0.5 mM to 100 mM, preferably 1.0 mM to 10 mM, and more preferably 2.0 mM to 5.0 mM, and the cell culture supernatant liquid containing EV in an amount of usually 0.1 ml to 100 ml, preferably 0.1 ml to 10 ml, and more preferably 0.1 ml to 1.0 ml per 1 mg of the insoluble carriers on which the PS-affinity substance is immobilized are brought into contact with each other at usually 4.0° C. to 37° C., preferably 4.0° C. to 25° C., and more preferably 4.0° C. to 11° C. for usually 0.5 to 24 hours, preferably 0.5 to 8.0 hours, and more preferably 0.5 to 4.0 hours, to form a composite body composed of the PS-affinity substance bonded to the carriers and the PS-positive extracellular vesicle in the cell culture supernatant liquid containing EV (composite body according to the present invention).

The composite body separation step may be any method as long as the composite body according to the present invention and the cell culture supernatant liquid containing EV can be separated from each other to obtain the composite body according to the present invention, and examples thereof include the following methods.

(1) In a case where in an insoluble carrier on which a PS-affinity substance is immobilized, the carrier is a magnetic carrier: a method of installing a container that contains the composite body according to the present invention obtained in the composite body formation step on a magnet stand, as necessary, aggregating the composite body according to the present invention on a tube wall by using magnetic force, and removing supernatant to separate the composite body from the cell culture supernatant liquid containing EV.

(2) In a case where in an insoluble carrier on which a PS-affinity substance is immobilized, the carrier in the form of a bead: a method of centrifuging a container that contains the composite body according to the present invention obtained in the composite body formation step, aggregating the composite body according to the present invention by precipitation, and removing supernatant to separate the composite body from the cell culture supernatant liquid containing EV.

(3) A method of separating the composite body according to the present invention from the cell culture supernatant liquid containing EV by filtration.

Specific examples of the composite body separation step include the following method: in a case where a magnetic carrier is used as an insoluble carrier, a method of installing a container that has been subjected to the composite body formation step on a magnet stand, as necessary, aggregating the obtained composite body according to the present invention on a tube wall by using magnetic force, and removing a supernatant specimen.

After the composite body separation step, as necessary, the obtained composite body according to the present invention may be washed with a calcium ion-containing washing solution (hereinafter, may be abbreviated as a "washing operation"). By the washing operation, impurities in a biological specimen such as cell-derived components adhering to a surface of the insoluble carrier on which the PS-affinity substance is immobilized can be removed. As a washing method, other than a calcium ion-containing washing solution being used, a washing method usually used in this field can be used.

The calcium ion-containing washing solution used in the washing operation may be any solution as long as the solution contains calcium ions of usually 0.5 to 100 mM, preferably 1 to 10 mM, more preferably 2 mM to 5 mM, and does not affect the bonding of the PS-positive extracellular vesicles and the PS-affinity substance immobilized on an insoluble carrier, and examples thereof include a buffer solution (for example, TBS, TBS-T, and HBS) that contains calcium ions of usually 0.5 mM to 100 mM, preferably usually 1 mM to 10 mM, more preferably usually 2 mM to 5 mM, that has a buffering action at pH 7.0 to pH 8.0, preferably at pH 7.2 to pH 7.6, and that does not precipitate calcium. A phosphate buffer is not preferable since the phosphate buffer and calcium are bonded to cause precipitation. A buffer agent concentration in these buffer solutions is usually appropriately selected from the range of 5 mM to 50 mM, preferably 10 mM to 30 mM, and the concentration in a case of containing NaCl is usually appropriately selected from the range of 100 mM to 200 mM, and preferably 140 mM to 160 mM. Saccharides, salts such as NaCl, surfactants, preservatives, proteins such as BSA, or the like may be contained in this solution as long as an amount thereof does not inhibit the bonding of the PS-positive extracellular vesicles and the PS-affinity substance immobilized on the insoluble carrier. Examples of the surfactants include Tween (trademark) 20 (FUJIFILM Wako Pure Chemical Corporation) and the like, and a concentration of a surfactant in the washing solution is usually 0.00001% to 0.2%, and preferably usually 0.0005% to 0.1%.

A specific example of the washing operation will be described as an example of a washing operation using magnetic particles as an insoluble carrier for immobilizing the PS-affinity substance. That is, the calcium ion-containing washing solution according to the present invention is added to the container containing the composite body according to the present invention obtained in the composite body separation step, and the mixture is stirred. Thereafter, the container is installed on a magnet stand, the composite body according to the present invention is aggregated on the tube wall using magnetic force, and the solution in the container is discarded. These washing operations may be repeated several times as needed.

The acquisition step may be any method as long as the PS-positive extracellular vesicles can be acquired from the composite body according to the present invention, and a method by which the calcium ion concentration is reduced is preferable. Examples of the method by which the calcium ion concentration is reduced include a method of using a calcium ion chelating agent. That is, after the composite body separation step, and as necessary, after the washing operation, the PS-positive extracellular vesicles may be separated from the composite body according to the present invention by the calcium ion chelating agent acting on calcium ions (calcium ions bonded to the composite body according to the present invention and calcium ions introduced from the solution containing the composite body according to the present invention) to chelate calcium ions in a reaction system to reduce an effective concentration of the calcium ions in the reaction system.

The calcium ion chelating agent used in this method may be any compound capable of chelating calcium ions, and examples thereof include ethylenediaminetetraacetic acid (EDTA), nitrilotriacetic acid (NTA), diethylenetriaminepentaacetic acid (DTPA), L-glutamic acid diacetic acid (GLDA), hydroxyethylethylenediaminetriacetic acid (HEDTA), ethylene glycol bis (β-aminoethyl ether)-N,N,N,N-tetraacetic acid (GEDTA), triethylenetetramine-N,N,N',N",N"',N"'-hexacetic acid (TTHA), 2-hydroxyethyliminodiacetic acid (HIDA), N,N-bis(2-hydroxyethyl)glycine (DHEG), trans-iz,2-diaminocyclohexane-N,N,N',N'-tetraacetic acid, monohydrate (CyDTA), and EDTA, GEDTA, CyDTA are preferable.

The calcium ion chelating agent is usually used as a solution. A solution for dissolving the calcium ion chelating agent may be any solution as long as the solution dissolves the calcium ion chelating agent, and examples thereof include purified water, a buffer solution, and the like. As the buffer solution, a buffer solution having a buffering action usually at pH 7.0 to pH 8.0, and preferably pH 7.2 to pH 7.6 (for example, PBS, TBS, HBS, or the like) is preferable. A buffer agent concentration in these buffer solutions is usually appropriately selected from the range of 5 mM to 50 mM, preferably 10 mM to 30 mM, and the concentration in a case of containing NaCl is usually appropriately selected from the range of 100 mM to 200 mM, and preferably 140 mM to 160 mM. The solution containing a calcium ion chelating agent (hereinafter, may be abbreviated as "calcium ion chelating agent-containing solution") may contain, for example, saccharides, salts such as NaCl, preservatives, proteins, and the like.

The concentration of the calcium ion chelating agent in the calcium ion chelating agent-containing solution is usually 0.5 mM to 500 mM, preferably 0.5 mM to 100 mM, and more preferably 0.5 mM to 50 mM. The pH of the calcium ion chelating agent-containing solution is usually pH 6.0 to pH 9.0, preferably pH 7.0 to pH 8.0, and more preferably pH 7.2 to pH 7.6.

In order to cause the calcium ion chelating agent to act on the calcium ions bonded to the composite body according to the present invention, the calcium ion chelating agent-containing solution is brought into contact with the composite body (for example, in the form of a pellet) according to the present invention to react the calcium ions bonded to the composite body according to the present invention with the calcium ion chelating agent in the calcium ion chelating agent-containing solution.

The calcium ion chelating agent-containing solution and the composite body according to the present invention can be brought into contact with each other by, for example, a method of suspending the composite body according to the present invention in the calcium ion chelating agent-containing solution (in the case where in an insoluble carrier on which the PS-affinity substance is immobilized, the insoluble carrier is a bead, or the like), a method of immersing the composite body according to the present invention in the calcium ion chelating agent-containing solution (in the case where in an insoluble carrier on which the PS-affinity substance is immobilized, the insoluble carrier is a disc-shaped piece, a tube, or the like), or the like.

As for the amount of the calcium ion chelating agent-containing solution to be brought into contact with the composite body according to the present invention, the amount by which the concentration of the calcium ions in the solution after being brought into contact with the composite body according to the present invention is less than the effective concentration, and the extracellular vesicles are separated from the composite body according to the present invention, may be adopted.

The temperature and time for allowing the calcium ion chelating agent to act (contact) on the composite body according to the present invention are usually 4.0° C. to 37° C., preferably 10° C. to 30° C., and more preferably 20° C. to 30° C., and usually 1 to 10 minutes, and preferably 5 to 15 minutes, respectively.

The acquisition step will be described with an example of a method using a carrier(Tim carrier) in which a Tim protein is bonded to an insoluble carrier, as follows. That is, after the composite body separation step is carried out, and as necessary, after the washing operation is further carried out, a solution containing the calcium ion chelating agent of usually 0.5 mM to 500 mM, preferably 0.5 mM to 100 mM, and more preferably 0.5 mM to 50 mM is added to the obtained composite body according to the present invention at usually 10 μL to 500 μL, preferably 20 μL to 200 μL, more preferably 50 μL to 100 μL per 1 mg of a Tim carrier, and the reaction is carried out at usually 4.0° C. to 37° C., preferably 10° C. to 30° C., and more preferably 20° C. to 30° C. for usually 1 to 30 minutes, preferably 5 to 15 minutes to separate PS-positive extracellular vesicles from the composite body according to the present invention.

By carrying out the acquisition step, the calcium ion chelating agent-containing solution brought into contact with the composite body according to the present invention contains the insoluble carrier on which the PS-affinity substance is immobilized and the extracellular vesicles separated (liberated) from the composite body according to the present invention. Therefore, in a case where the carrier on which the PS-affinity substance is immobilized is removed from the solution, and only the solution is recovered, a solution containing PS-positive extracellular vesicles can be obtained.

The PS-positive extracellular vesicles thus prepared effectively suppressed the production of inflammatory cytokines. Therefore, the anti-inflammatory agent provided in the present invention is based on an inhibitory action of PS-positive extracellular vesicles as an active ingredient on the production of inflammatory cytokines. The inflammatory cytokines are substances produced from lymphocytes, macrophages, and the like, and involved in inflammatory reactions associated with bacterial and viral infections, tumors, and tissue damage. For example, inflammatory cytokines such as interleukin-1β (IL-1β), interleukin-6 (IL-6), and tumor necrosis factor (TNF-α) originally have purposeful functions such as activation of immune functions against invasion by pathogenic bacteria, but it is known that when continuously overproduced due to certain causes, they can cause a variety of inflammatory diseases such as rheumatoid arthritis, ulcerative colitis, Crohn's disease, type 2 diabetes, and obesity (especially insulin resistance).

The present invention is to provide the anti-inflammatory agent that suppresses the production of inflammatory cytokines exhibited by the PS-positive extracellular vesicles, and that is effective on inflammatory diseases such as rheumatoid arthritis, ulcerative colitis, Crohn's disease, and type 2 diabetes, which are caused by overproduction of these inflammatory cytokines.

The anti-inflammatory agent provided in the present invention basically contains the PS-positive extracellular vesicles acquired by isolation from the MSC-derived extracellular vesicles according to the present invention as an active ingredient, and the dosage form for administration is a solution containing PS-positive extracellular vesicles as is, or a form formulated as a liquid agent, a suspending agent, a lipo agent, or the like with a pharmaceutically acceptable carrier as needed and an additive, or furthermore, a form formulated as a solid agent such as a tablet with a pharmaceutically acceptable additive, as a powder by freeze-drying.

Examples of such carriers and additives include tonicity adjusting agents, thickeners, saccharides, sugar alcohols, antiseptics (preservatives), bactericides or antibacterial agents, pH adjusters, stabilizers, chelating agents, oleaginous bases, gel bases, surfactants, suspending agents, bonding agents, excipients, lubricants, disintegrants, foaming agents, fluidizing agents, dispersants, emulsifiers, buffers, solubilizing agents, antioxidants, sweeteners, acidulating agents, colorants, flavoring agents, perfumes, and cooling agents, but not limited thereto.

Examples of typical carriers, additives, and the like can include the following. Examples of the carriers include an aqueous carrier such as water and hydrous ethanol. Examples of the tonicity adjusting agents include inorganic salts such as sodium chloride, potassium chloride, calcium chloride, and magnesium chloride. Examples of the polyhydric alcohols include glycerin, propylene glycol, polyethylene glycol, and the like. Examples of the thickeners include carboxyvinyl polymer, hydroxyethyl cellulose, hydroxypropylmethyl cellulose, methyl cellulose, alginic acid, polyvinyl alcohol (completely or partially saponified), polyvinylpyrrolidone, macrogol, and the like.

Examples of the saccharides include cyclodextrin, glucose, fructose, lactose, and the like. Examples of sugar alcohols include sugar alcohols such as xylitol, sorbitol, and mannitol. Examples of antiseptics, bactericides, or antibacterial agents include dibutylhydroxytoluene, benzalkonium chloride, benzethonium chloride, chlorhexidine gluconate, sodium dehydroacetate, methyl paraoxybenzoate, ethyl paraoxybenzoate, propyl paraoxybenzoate, butyl sugar paraoxybenzoate. Examples of the pH adjusters include hydrochloric acid, boric acid, aminoethylsulfonic acid, citric acid, acetic acid, sodium hydroxide, potassium hydroxide, calcium hydroxide, magnesium hydroxide, sodium hydrogencarbonate, sodium carbonate, borosand, triethanolamine, monoethanolamine, diisopropanolamine, sulfuric acid, magnesium sulfate, phosphoric acid, polyphosphate, propionic acid, oxalic acid, gluconic acid, fumaric acid, lactic acid, tartaric acid, malic acid, succinic acid, and the like.

Examples of the stabilizers include dibutylhydroxytoluene, trometamol, sodium formaldehyde sulfoxylate (rongalite), tocopherol, sodium pyrosulfite, monoethanolamine, aluminum monostearate, glycerin monostearate, sodium hydrogen sulfite, sodium sulfite, and the like. Examples of the bases include vegetable oils such as olive oil, corn oil, soybean oil, sesame oil, and cottonseed oil; oleaginous bases such as medium-chain fatty acid triglycerides; aqueous bases such as Macrogol 400; gel bases such as carboxyvinyl polymers and gums. Examples of the surfactants include polysorbate 80, hardened castor oil, glycerin fatty acid ester, sorbitan sesquioleate, and the like, and examples of the suspending agents include white beeswax and various surfactants, gum arabic, gum arabic powder, xanthan gum, soy lecithin, and the like.

Furthermore, examples of the bonding agents include hydroxyethyl cellulose, hydroxypropyl cellulose, hydroxypropylmethyl cellulose, sodium carboxymethyl cellulose, polyvinylpyrrolidone, polyvinyl alcohol, and the like, examples of the excipients include sucrose, lactose, starch, corn starch, crystalline cellulose, light anhydrous silicic acid, and the like, examples of the lubricants include sucrose fatty acid ester, magnesium stearate, talc, and the like, examples of the disintegrants include low-substituted hydroxypropyl cellulose, crospovidone, croscarmellose sodium, and the like, and examples of the fluidizing agents include sodium aluminometasilicate, light anhydrous silicic acid, and the like.

The anti-inflammatory agent provided in the present invention is preferably formulated as a liquid agent, a suspending agent, or a lipo agent, and is basically obtained by mixing the solution containing the PS-positive extracellular vesicles isolated from MSC-derived extracellular vesicles according to the present invention with, for example, saline, 5% glucose solution, lipo emulsion, or the like together with the above described carriers and additives, as necessary. In addition, freeze-dried powder can be used for dissolution before use or the suspension-type preparation.

In a case where the anti-inflammatory agent provided in the present invention is a liquid agent, a suspending agent, or a lipo agent, the pH of the anti-inflammatory agent is not particularly limited as long as the pH thereof is within a pharmaceutically, pharmacologically or physiologically acceptable range, and examples of the range include a range of pH 2.5 to 9.0, preferably 3.0 to 8.5, and more preferably 3.5 to 8.0, and the pH can be adjusted appropriately with a pH adjuster.

An administration route of the anti-inflammatory agent provided in the present invention includes oral administration, subcutaneous administration, intramuscular administration, intravenous administration, intraarterial administration, intrathecal administration, and intraperitoneal administration, depending on the dosage form. Although the dose varies depending on a condition of a target patient (body weight, age, symptoms, physical condition, and the like), dosage form, and the like, the number of particles is usually $1\times10^5$ to $1\times10^{17}$ pieces/time, preferably $5\times10^5$ to $5\times10^{16}$ pieces/time, still more preferably $1\times10^6$ to $1\times10^{16}$ pieces/time, and particularly preferably $5\times10^6$ to $5\times10^{15}$ pieces/time but in a case of the administration to an adult. This dose may be used as a single dose and may be administered multiple times a day, and this dose may be divided into a plurality of times and administered.

EXAMPLES

Hereinafter, the present invention will be specifically described based on Examples and Comparative Examples, but the present invention is not limited to these examples.

Example 1: Acquisition of Extracellular Vesicle by PS-Affinity Method (1) Cell Culture Poietics (trademark) huma mesenchymal stem cells (Lonza.), which are bone marrow-derived mesenchymal stem cells, were cultured in MEMα (L-glutamine, phenol red contained, FUJIFILM Wako Pure Chemical Corporation) containing 15% FBS (Selborne Biological Services Pty. Co., Ltd.) used as a proliferated culture medium. Thereafter, the cultured bone marrow-derived mesenchymal stem cells were seeded in a 100 mm cell culture dish (Corning Incorporated) with a cell count of $3\times10^5$, cultured in a cell culture incubator set under conditions of 5% $CO_2$ and 37° C. for 72 hours, and proliferated to a cell count of $3\times10^6$.

(2) Production of Extracellular Vesicle

The culture medium was substituted with 20 mL D-MEM (FUJIFILM Wako Pure Chemical Corporation) containing 10% GIBCO, extracellular vesicle production culture medium: Fetal Bovine Serum, exosome-depleted, One Shot (trademark) format (Thermo Fisher Scientific Inc.), and the bone marrow-derived mesenchymal stem cells proliferated in (1) were cultured in a cell culture incubator set under conditions of 5% $CO_2$ and 37° C. for 120 hours. Thereafter, the obtained culture supernatant was recovered into a 50 mL centrifuge tube and centrifuged at 2,000×g for 20 minutes, and the supernatant was recovered.

(3) Acquisition of Extracellular Vesicle by PS-Affinity Method

Extracellular vesicles were isolated from 1 mL of the culture supernatant recovered in (2) using MagCapture (trademark) Exosome Isolation Kit PS (FUJIFILM Wako Pure Chemical Corporation) according to a procedure described in the instruction manual attached to the kit to obtain extracellular vesicles in 1 mM EDTA-containing phosphate-buffered saline (PBS) to which an EV-Save (trademark) extracellular vesicle blocking reagent (FUJIFILM Wako Pure Chemical Corporation) was added. Thereafter, the buffer was exchanged with PBS to which EV-Save (trademark) extracellular vesicle blocking reagent was added, by using Vivaspin 500 (Sartorius AG, molecular weight cut-off: 100,000 (100K), membrane material: PES). Hereinafter, the obtained solution may be referred to as an "extracellular vesicle solution (PS-affinity method, bone marrow-derived MSC)".

Comparative Example 1. Acquisition of Extracellular Vesicle by Ultracentrifugal Method The culture supernatant prepared according to the same method as in Example 1(1) and (2) was centrifuged at 110,000×g for 70 minutes, by using an ultracentrifuge (Beckman: Optima (trademak) L-100XP). As a result, pellets were obtained, 1 mL of PBS was added to the obtained pellets, and the mixture was centrifuged again at 110,000×g for 70 minutes. The finally obtained pellets were dissolved with PBS to which an EV-Save (trademark) extracellular vesicle blocking reagent was added (FUJIFILM Wako Pure Chemical Corporation). Hereinafter, the obtained solution may be referred to as an "extracellular vesicle solution (ultracentrifugal method, bone marrow-derived MSC)".

Experimental Example 1. Measurement of the Number of Particles of Extracellular Vesicles by Nanotracking Analysis Method The number of particles of the "extracellular vesicle solution (PS-affinity method, bone marrow-derived MSC)" obtained in Example 1 per unit volume was measured by a nanoparticle tracking analysis method (nanotracking analysis method) using NanoSight (Malvern Panalytical Ltd) according to a procedure described in the manual of NanoSight, and an average particle size and an average number of particles per unit volume [particles/mL] were calculated. A graph of the obtained particle size distribution is illustrated in FIG. 1 together with the results of Experimental Example 2. In the graph of FIG. 1, the vertical axis indicates the number of particles, and the horizontal axis indicates the particle size. The average particle size of the extracellular vesicles acquired by the PS-affinity method was 138.1±0.2 nm, and the average number of particles per unit volume was $1.76\times10^{10}$ [particles/mL].

Experimental Example 2. Measurement of The Number of Particles of Extracellular Vesicles by Nanotracking Analysis Method An average particle size and an average number of particles per unit volume [particles/mL] were calculated according to the same method as in Experimental Example 1, except that the "extracellular vesicle solution (ultracentrifugal method, bone marrow-derived MSC)" obtained in Comparative Example 1 was used instead of the "extracellular vesicle solution (PS-affinity method, bone marrow-derived MSC)". A graph of the obtained particle size distribution is illustrated in FIG. 1 together with the results of Experimental Example 1. The average particle size of the extracellular vesicles acquired by the ultracentrifugal method was 138.1±2.9 nm, and the average number of particles per unit volume was $1.68\times10^{10}$ [particles/mL].

Experimental Example 3. Analysis of Extracellular Vesicle Marker Protein by Western Blotting Method Extracellular vesicle marker proteins CD9, CD63, and CD81 were analyzed by a Western blotting method by using the "extracellular vesicle solution (PS-affinity method, bone marrow-derived MSC)" obtained in Example 1.

Figures 2, 3:
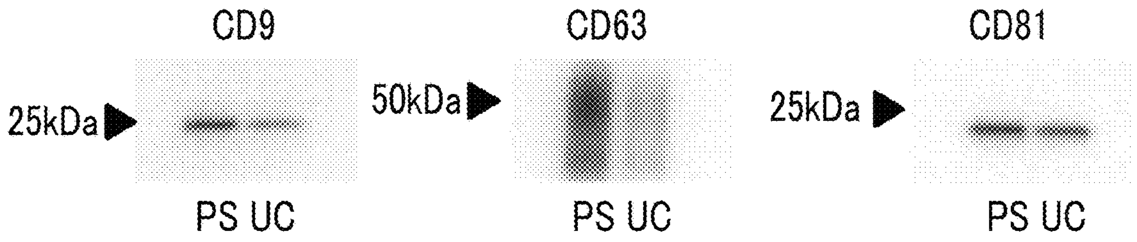
FIG. 2 is a diagram illustrating results of detecting CD9, CD63, and CD81 of MSC-derived extracellular vesicles acquired by the PS-affinity method and the ultracentrifugal method by a Western blotting method.
FIG. 3 is a diagram illustrating primers used for quantitative PCR.

Based on the average number of particles per unit volume in the "extracellular vesicle solution (PS-affinity method, bone marrow-derived MSC)" calculated in Experimental Example 1, ¼ amount of SDS-PAGE Sample Buffer 4-fold concentrated solution (without a reducing agent) was mixed with $3.0\times10^{8}$ particles of the "extracellular vesicle solution (PS-affinity method, bone marrow-derived MSC)" (FUJIFILM Wako Pure Chemical Corporation), and the total amount was subjected to electrophoresis on a 10% to 20% acrylamide gel (FUJIFILM Wako Pure Chemical Corporation). Thereafter, the transcription was carried out to a PVDF membrane (Bio-Rad Laboratories, Inc.) by using a transfer buffer (FUJIFILM Wako Pure Chemical Corporation). The transferred membrane was immersed in a PBS-T solution containing 1% skim milk (0.1 (w/v) % Tween (trademark) 20-containing PBS solution) for 1 hour and was subjected to blocking treatment, and each of anti-CD9 antibodies (FUJIFILM Wako Pure Chemical Corporation), anti-CD63 antibodies (FUJIFILM Wako Pure Chemical Corporation), and anti-CD81 antibodies (FUJIFILM Wako Pure Chemical Corporation) was allowed to react with a primary antibody solution adjusted to 1.1 μg/mL with a PBS-T solution. Thereafter, the membrane on which the anti-CD9 antibodies and the anti-CD81 antibodies had reacted was allowed to react with a secondary antibody solution obtained by diluting HRP-flagged anti-rat IgG antibodies (Jackson ImmunoResearch Inc.) to 10,000 times with a PBS-T solution, and the membrane on which the anti-CD63 antibodies had reacted was allowed to react with a secondary antibody solution obtained by diluting HRP-flagged anti-mouse IgG antibodies (Agilent Technologies, Inc.) with a PBS-T solution to 10,000 times. Thereafter, Immunostar (trademark) Zeta (FUJIFILM Wako Pure Chemical Corporation) was used as a detection reagent to detect a signal by using Amersham Imager 600 (General Electric Company). The results of Western blotting are illustrated in FIG. 2 together with the results of Experimental Example 4. In the figure, PS on the horizontal axis represents the result in a case where the "extracellular vesicle solution (PS-affinity method, bone marrow-derived MSC)" is used (Experimental Example 3), and UC represents the result in a case where the "extracellular vesicle solution (ultracentrifugal method, bone marrow-derived MSC)" is used (Experimental Example 4). The arrows on the vertical axis indicate band positions of the detected extracellular vesicle marker proteins.

Experimental Example 4. Analysis of Extracellular Vesicle Marker Protein by Western Blotting Method Extracellular vesicle marker proteins CD9, CD63, and CD81 were analyzed by a Western blotting method according to the same method as in Experimental Example 3, except that the "extracellular vesicle solution (ultracentrifugal method, bone marrow-derived MSC)" obtained in Comparative Example 1 was used instead of the "extracellular vesicle solution (PS-affinity method, bone marrow-derived MSC)". The result of Western blotting is illustrated in FIG. 2 together with the result of Experimental Example 3.

It was found from FIG. 2 that expression levels of CD9 and CD63 of the extracellular vesicles acquired by the PS-affinity method [extracellular vesicles in the "extracellular vesicle solution (PS-affinity method, bone marrow-derived MSC)", Experimental Example 3] were higher than those of the extracellular vesicles [extracellular vesicles in the "extracellular vesicle solution (ultracentrifugal method, bone marrow-derived MSC)", Experimental Example 4] obtained by the ultracentrifugal method.

Examples 2 to 4: Evaluation of Anti-inflammatory Action of Extracellular Vesicle Acquired by PS-Affinity Method The anti-inflammatory action of the extracellular vesicles in the "extracellular vesicle solution (PS-affinity method, bone marrow-derived MSC)" prepared in Example 1 was evaluated.

Peripheral blood mononuclear cells (PBMCs FUJIFILM Wako Pure Chemical Corporation), which are human peripheral blood mononuclear cells, were suspended in RPMI (FUJIFILM Wako Pure Chemical Corporation) containing 10% FBS (Biosera) and were seeded into 48-well plate (Thermo Fisher Scientific Inc.) with a cell count of $5\times10^5$ per well and a medium volume of 250 μL. Two hours after cell seeding, the cells were washed with 250 μL of phosphate-buffered saline (PBS, FUJIFILM Wako Pure Chemical Corporation), and non-adherent cells were removed.

Next, the "extracellular vesicle solution (PS-affinity method, bone marrow-derived MSC)" obtained in Example 1 was mixed with RPMI (FUJIFILM Wako Pure Chemical Corporation) containing 10% FBS (Biosera) to obtain a solution, and the obtained solution was added to the 48-well plate from which the non-adherent cells were removed in an amount of the number of particles of $1\times10^8$ per well, and was cultured for 16 hours. Thereafter, lipo poly saccharide (LPS, FUJIFILM Wako Pure Chemical Corporation) was added to each well so as to have a final concentration of 100 ng/mL. After culturing for 4 hours, each RNA was extracted by using a PureLink (trademark) RNA Mini kit (Thermo Fisher Scientific Inc.) according to the procedure described in the instruction manual attached to the kit. From 20 ng of the extracted RNA, cDNA was synthesized by using RiverTra Ace (trademark) qPCR RT Master Mix with gDNA Remover (Toyobo Co., Ltd.) according to the procedure described in the instruction manual attached to the kit.

A mRNA expression level of each of the inflammatory cytokines TNFα (Example 2), IL-6 (Example 3), the anti-inflammatory cytokine TGFβ1 (Example 4), and the internal standard GAPDH was measured by quantitative PCR, by KOD SYBR qPCR Mix (Toyobo Co., Ltd.) using the synthesized cDNA. Each of primers used for quantitative PCR is illustrated in FIG. 3 (SEQ ID NO. 1 to 6).

Figure 4:
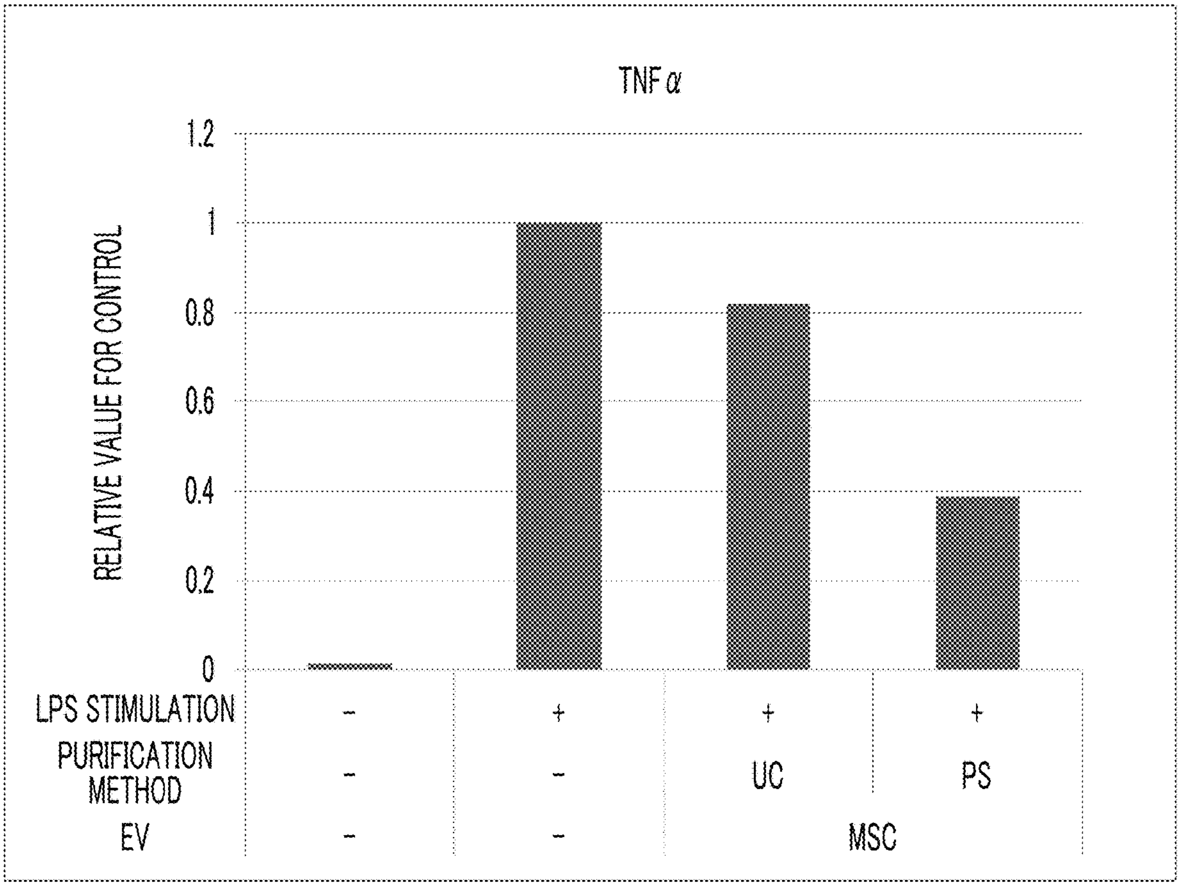
FIG. 4 is a diagram illustrating a result of evaluating an anti-inflammatory action of bone marrow MSC-derived extracellular vesicles using a mRNA expression level of TNFα as an index.
Figure 5:
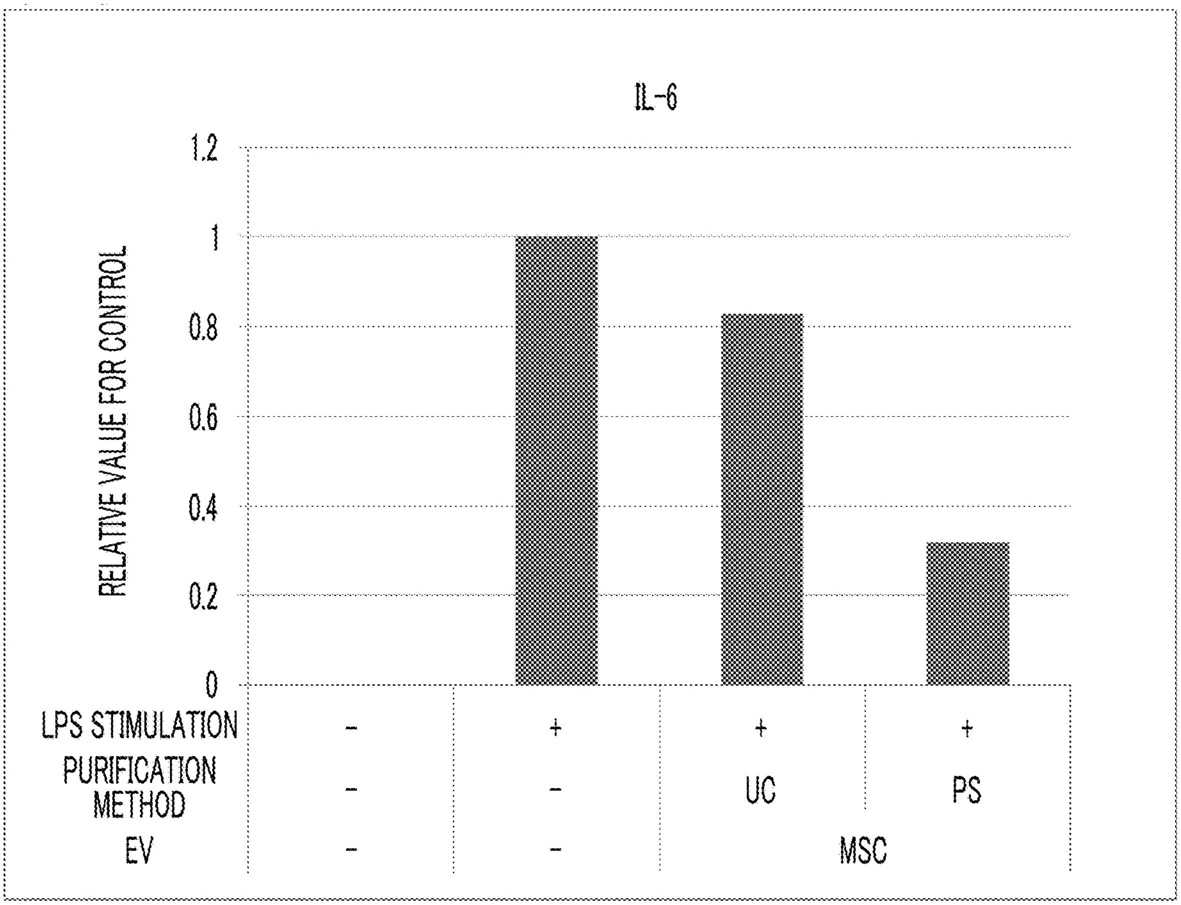
FIG. 5 is a diagram illustrating a result of evaluating an anti-inflammatory action of bone marrow MSC-derived extracellular vesicles using a mRNA expression level of IL-6 as an index.
Figure 6:
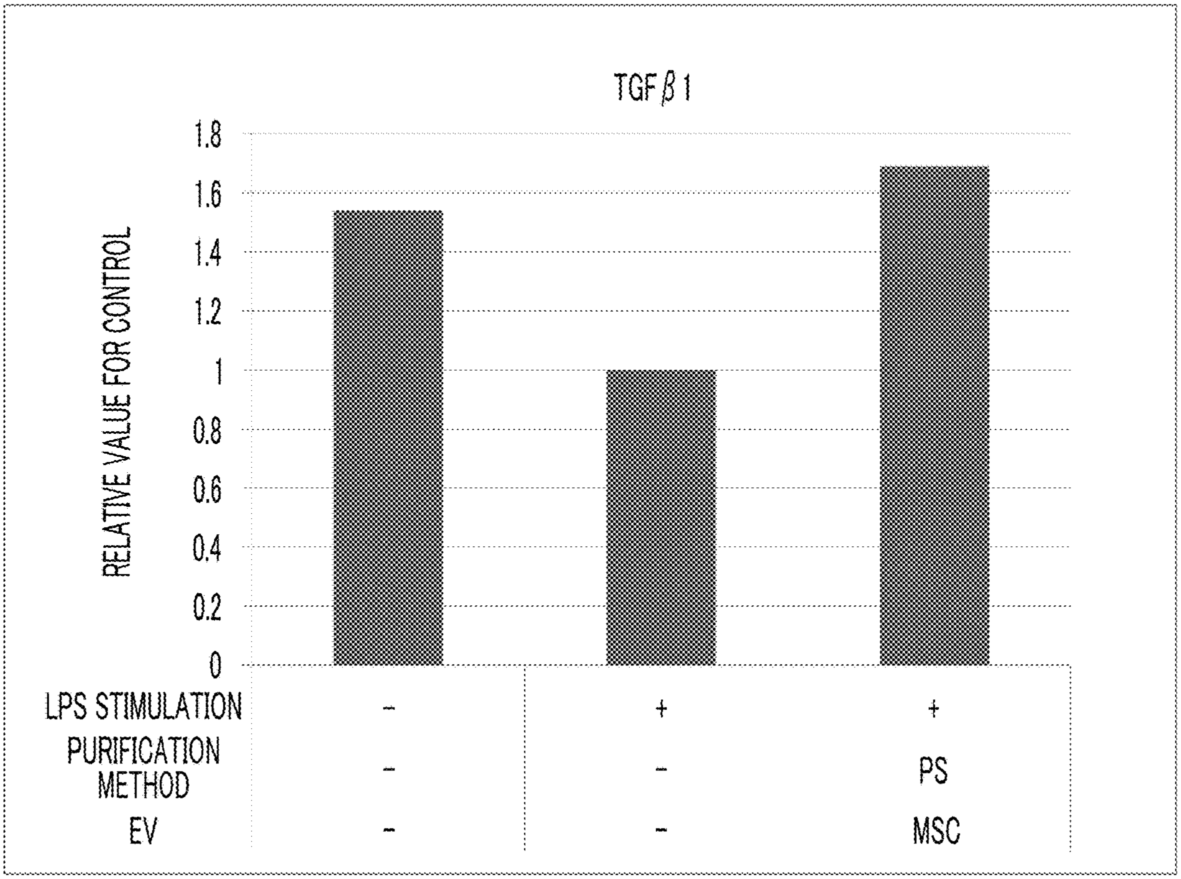
FIG. 6 is a diagram illustrating a result of evaluating an anti-inflammatory action of bone marrow MSC-derived extracellular vesicles using a mRNA expression level of TGFβ1 as an index.

The results of quantitative PCR are illustrated in FIGS. 4 to 6 together with the results of Comparative Examples 2 to 4. FIG. 4 illustrates the mRNA expression level of TNFα that is an inflammation-related protein, FIG. 5 illustrates the mRNA expression level of IL-6, and FIG. 6 illustrates the result of the mRNA expression level of TGF1. In the figures, in the horizontal axis, "LPS STIMULATION (−), PURIFICATION METHOD (−), EV (−)" illustrates the result in PBMC to which stimulation was not applied, "LPS STIMULATION (+), PURIFICATION METHOD (−), EV (−)" illustrates the result in PBMC (control) to which LPS stimulation was applied, "LPS STIMULATION (+), PURIFICATION METHOD (PS), EV (MSC)" illustrates the result in a case where the "extracellular vesicle solution (PS-affinity method, bone marrow-derived MSC) was used to PBMC to which LPS stimulation was applied (Example 2 (FIG. 4), Example 3 (FIG. 5), and Example 4 (FIG. 6)), and "LPS STIMULATION (+), PURIFICATION METHOD (UC), EV (MSC)" illustrates the result in a case where the "extracellular vesicle solution (ultracentrifugal method, bone marrow-derived MSC)" was used to PBMC to which LPS stimulation was applied (Comparative Example 2 (FIG. 4) and Comparative Example 3 (FIG. 5)). As for the expression level of each gene, the numerical value obtained from qPCR performed with the primer for each gene was normalized to GAPDH, illustrated as the ΔΔct value relative to the expression of the target mRNA in the control, and illustrated on the vertical axis of each figure.

Comparative Examples 2 and 3. Evaluation of Anti-inflammatory Action of Extracellular Vesicle Acquired by Ultracentrifugal Method A mRNA expression level of each of the inflammatory cytokines TNFα (Comparative Example 2), IL-6 (Comparative Example 3), and the internal standard GAPDH was measured by quantitative PCR according to the same method as in Examples 2 and 3, except that the "extracellular vesicle solution (ultracentrifugal method, bone marrow-derived MSC)" obtained in Comparative Example 1 was used instead of the "extracellular vesicle solution (PS-affinity method, bone marrow-derived MSC)", to evaluate the anti-inflammatory action of the extracellular vesicles. The results of quantitative PCR are illustrated in FIGS. 4 and 5 together with the results of Examples 2 to 4.

It was found from FIGS. 4 and 5 that in the case where the extracellular vesicles acquired by the PS-affinity method were used (Examples 2 and 3), an increase in the mRNA expression level of each of the inflammatory cytokines TNFα (FIG. 4) and IL-6 (FIG. 5) was suppressed due to LPS stimulation (having the anti-inflammatory action). It was found from FIG. 6 that in the case where the extracellular vesicles acquired by the PS-affinity method were used (Example 4), a decrease in the mRNA expression level of the anti-inflammatory cytokine TGFβ1 (FIG. 6) was suppressed due to LPS stimulation (having the anti-inflammatory action). In addition, it was found that the extracellular vesicles acquired by the PS-affinity method (Examples 2 to 4) have a remarkably higher anti-inflammatory action than the extracellular vesicles acquired by the ultracentrifugal method (Comparative Examples 2 and 3).

Examples 5 and 6: Acquisition of Extracellular Vesicle by PS-affinity Method

Extracellular vesicles were acquired by the same method as in Example 1 except that "huma mesenchymal stem cells from umbilical cord matrix (PromoCell GmbH), which are umbilical cord-derived mesenchymal stem cells" (Example 5) or "human adipose-derived stem cells that are adipose-derived mesenchymal stem cells (Lonza.)" (Example 6) was used instead of "Poietics (trademark) huma mesenchymal stem cells that are bone marrow-derived mesenchymal stem cells (Lonza.)", and an "extracellular vesicle solution (PS-affinity method, umbilical cord-derived MSC)" (Example 5) and an "extracellular vesicle solution (PS-affinity method, adipose-derived MSC)" (Example 6) were individually obtained.

Comparative Examples 4 and 5. Acquisition of Extracellular Vesicle by Ultracentrifugal Method Culture supernatant prepared according to the same method as in Example 1(1) and (2) was centrifuged by using an ultracentrifuge (Beckman: Optima (trademark) L-100XP) at 110,000×g for 70 minutes, except that "huma mesenchymal stem cells from umbilical cord matrix (PromoCell GmbH), which are umbilical cord-derived mesenchymal stem cells" (Comparative Example 4) or "human adipose-derived stem cells (Lonza.) that are adipose-derived mesenchymal stem cells" (Comparative Example 5) was used instead of "Poietics (trademark) huma mesenchymal stem cells that are bone marrow-derived mesenchymal stem cells (Lonza.). As a result, pellets were obtained, 1 mL of PBS was added to the obtained pellets, and the mixture was centrifuged again at 110,000×g for 70 minutes. The finally obtained pellets were dissolved with PBS to which an EV-Save (trademark) extracellular vesicle blocking reagent was added (FUJIFILM Wako Pure Chemical Corporation), and an "extracellular vesicle solution (ultracentrifugal method, umbilical cord-derived MSC)" (Comparative Example 4) and an "extracellular vesicle solution (ultracentrifugal method, adipose-derived MSC)" (Comparative Example 5) were individually obtained.

Examples 7 to 12: Evaluation of Anti-Inflammatory Action of Extracellular Vesicle Acquired by PS-Affinity Method The anti-inflammatory action of the extracellular vesicles in the "extracellular vesicle solution (PS-affinity method)" prepared in each of Examples 5 and 6 was evaluated. Peripheral blood mononuclear cells (PBMCs FUJIFILM Wako Pure Chemical Corporation), which are human peripheral blood mononuclear cells, were suspended in RPMI (FUJIFILM Wako Pure Chemical Corporation) containing 10% FBS (Biosera) and were seeded into 96-well plate (Thermo Fisher Scientific Inc.) with a cell count of $4\times10^5$ per well and a medium volume of 100 μL. Two hours after cell seeding, the cells were washed with 200 μL of phosphate-buffered saline (PBS, FUJIFILM Wako Pure Chemical Corporation), and non-adherent cells were removed.

Next, the "extracellular vesicle solution (PS-affinity method, umbilical cord-derived MSC)" (Examples 7, 9, and 11) obtained in Example 5 or the "extracellular vesicle solution (PS-affinity method, adipose-derived MSC)" (Examples 8, 10, and 12) obtained in Example 6 was mixed with RPMI (FUJIFILM Wako Pure Chemical Corporation) containing 10% FBS (Biosera) to obtain a solution, and the obtained solution was added to the 96-well plate from which the non-adherent cells were removed in an amount of the number of particles $1\times10^8$ per well, and was cultured for 16 hours. Thereafter, lipo poly saccharide (LPS, FUJIFILM Wako Pure Chemical Corporation) was added to each well so as to have a final concentration of 100 ng/mL. After culturing for 4 hours, each RNA was extracted by using a PureLink (trademark) RNA Mini kit (Thermo Fisher Scientific Inc.) according to the procedure described in the instruction manual attached to the kit. From 20 ng of the extracted RNA, cDNA was synthesized by using RiverTra Ace (trademark) qPCR RT Master Mix with gDNA Remover (Toyobo Co., Ltd.) according to the procedure described in the instruction manual attached to the kit.

A mRNA expression level of each of the inflammatory cytokines TNFα (Examples 7 and 8), IL-6 (Examples 9 and 10), the anti-inflammatory cytokine TGFβ1 (Examples 11 and 12), and the internal standard GAPDH was measured by quantitative PCR, by KOD SYBR qPCR Mix (Toyobo Co., Ltd.) using the synthesized cDNA. Each of primers used for quantitative PCR is illustrated in FIG. 3 (SEQ ID NO. 1 to 6).

Figure 7:
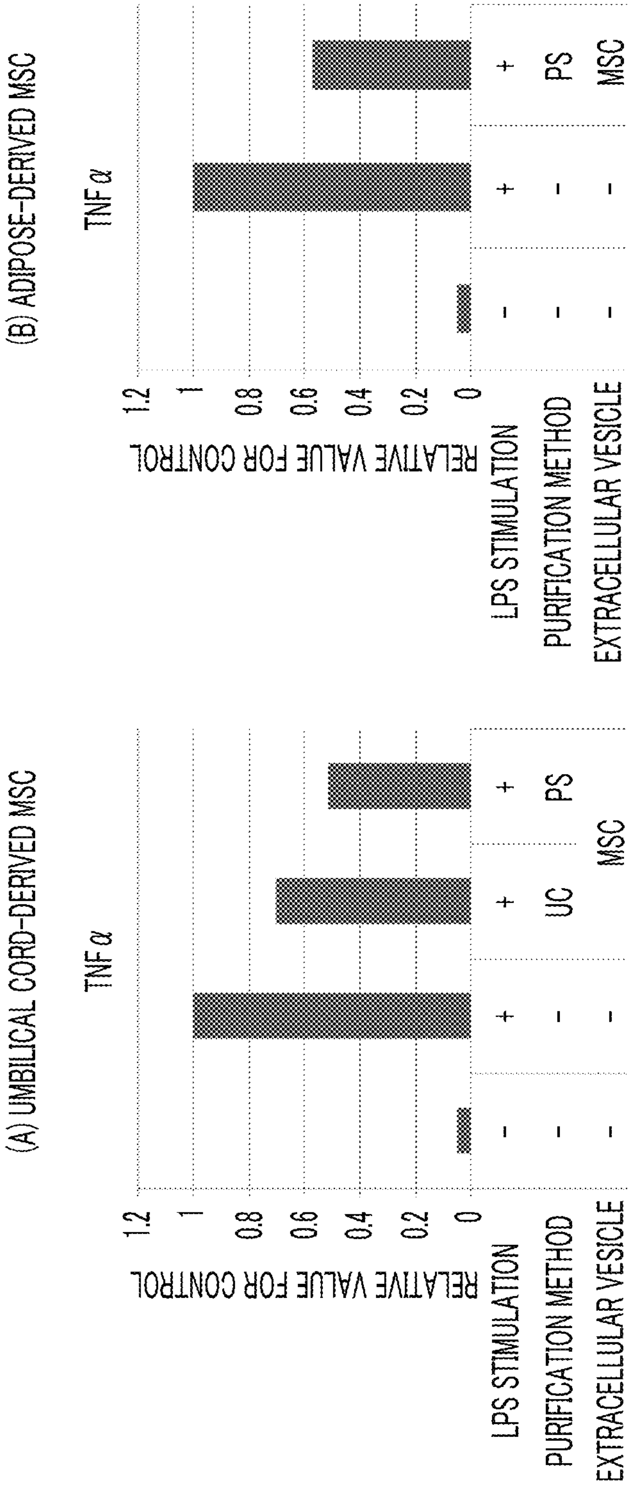
FIG. 7 is a diagram illustrating a result of evaluating an anti-inflammatory action of umbilical cord MSC-derived extracellular vesicles and adipose MSC-derived extracellular vesicles using a mRNA expression level of TNFα as an index.
Figure 8:
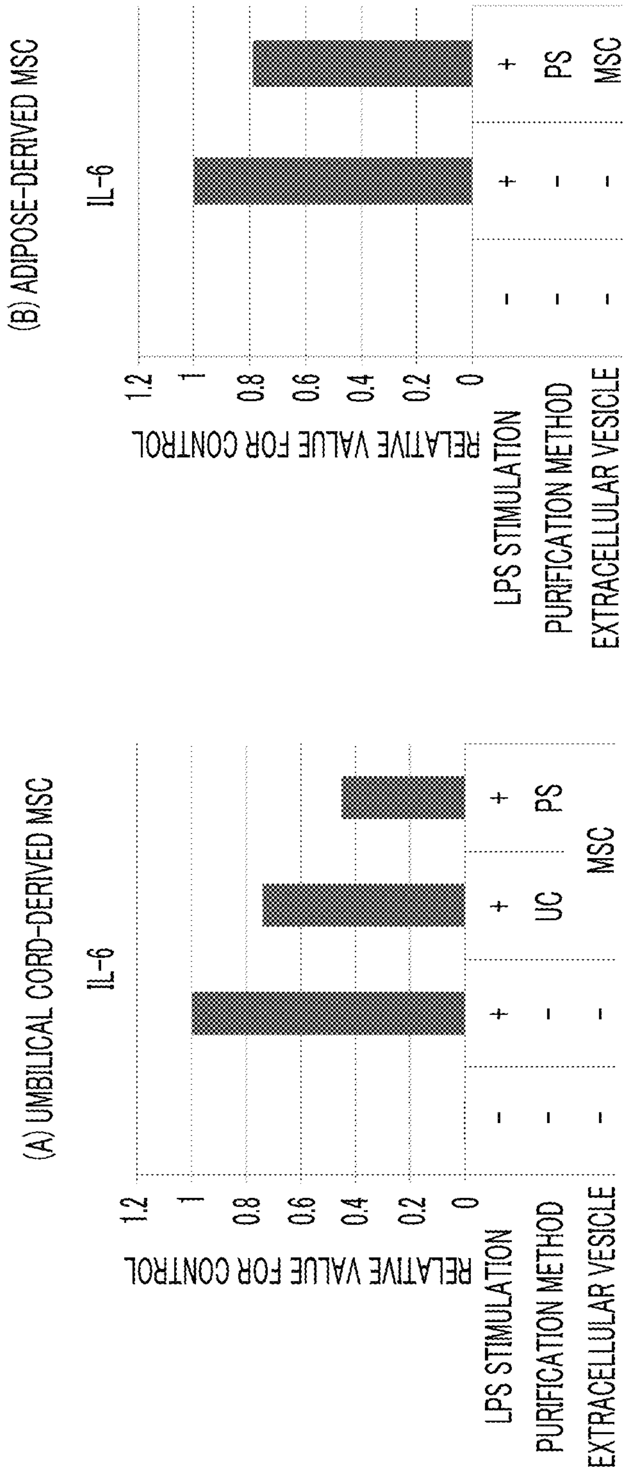
FIG. 8 is a diagram illustrating a result of evaluating an anti-inflammatory action of umbilical cord MSC-derived extracellular vesicles and adipose MSC-derived extracellular vesicles using a mRNA expression level of IL-6 as an index.
Figure 9:
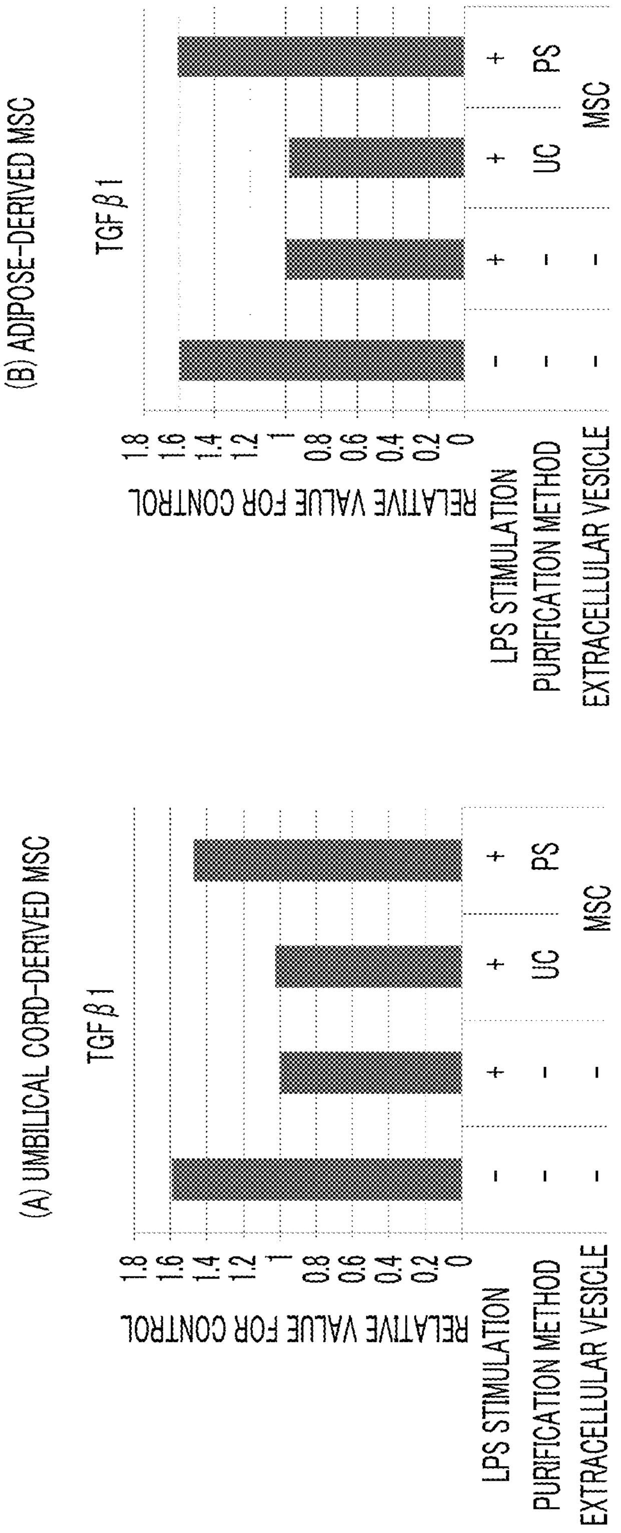
FIG. 9 is a diagram illustrating a result of evaluating an anti-inflammatory action of umbilical cord MSC-derived extracellular vesicles and adipose MSC-derived extracellular vesicles using a mRNA expression level of TGFβ1 as an index.

The results of quantitative PCR are illustrated in FIGS. 7 to 9 together with the results of Comparative Examples 6 to 9. FIG. 7 illustrates the mRNA expression level of TNFα that is an inflammation-related protein, FIG. 8 illustrates the mRNA expression level of IL-6, and FIG. 9 illustrates the result of the mRNA expression level of TGFβ1. In the figures, "(A) UMBILICAL CORD-DERIVED MSC" is the result in a case where the "extracellular vesicle solution (PS-affinity method, umbilical cord-derived MSC)" obtained in Example 5 or the "extracellular vesicle solution (ultracentrifugal method, umbilical cord-derived MSC)" obtained in Comparative Example 4 was used, and "(B) ADIPOSE-DERIVED MSC" is the result in a case where the "extracellular vesicle solution (PS-affinity method, adipose-derived MSC)" obtained in Example 6 or the "extracellular vesicle solution (ultracentrifugal method, adipose-derived MSC)" obtained in Comparative Example 5 was used. In the horizontal axis, "LPS STIMULATION (−), PURIFICATION METHOD (−), EXTRACELLULAR VESICLE (−)" illustrates the result in PBMC to which stimulation was not applied, "LPS STIMULATION (+), PURIFICATION METHOD (−), EXTRACELLULAR VESICLE (−)" illustrates the result in PBMC (control) to which LPS stimulation was applied, "LPS STIMULATION (+), PURIFICATION METHOD (UC), EXTRACELLULAR VESICLE (MSC)" illustrates the result in a case where the "extracellular vesicle solution (ultracentrifugal method)" was used to PBMC to which LPS stimulation was applied [Comparative Example 6 (FIG. 7, umbilical cord-derived MSC), Comparative Example 7 (FIG. 8, umbilical cord-derived MSC), Comparative Example 8 (FIG. 9, umbilical cord-derived MSC), and Comparative Example 9 (FIG. 9, adipose-derived MSC)), and "LPS STIMULATION (+), PURIFICATION METHOD (PS), EXTRACELLULAR VESICLE (MSC)" illustrates the result in a case where the "extracellular vesicle solution (PS-affinity method)" was used to PBMC to which LPS stimulation was applied [Example 7 (FIG. 7, umbilical cord-derived MSC), Example 8 (FIG. 7, adipose-derived MSC), Example 9 (FIG. 8, umbilical cord-derived MSC), Example 10 (FIG. 8, adipose-derived MSC), Example 11 (FIG. 9, umbilical cord-derived MSC), and Example 12 (FIG. 9, adipose-derived MSC)]. As for the expression level of each gene, the numerical value obtained from qPCR performed with the primer for each gene was normalized to GAPDH, illustrated as the ΔΔct value relative to the expression of the target mRNA in the control, and illustrated on the vertical axis of each figure.

Comparative Examples 6 to 9. Evaluation of Anti-inflammatory Action of Extracellular Vesicle Acquired by Ultracentrifugal Method A mRNA expression level of each of the inflammatory cytokines TNFα (Comparative Example 6), IL-6 (Comparative Example 7), TGFβ1 (Comparative Examples 8 and 9), and the internal standard GAPDH was measured by quantitative PCR according to the same method as in Examples 7 to 12, except that the "extracellular vesicle solution (ultracentrifugal method, umbilical cord-derived MSC)" obtained in Comparative Example 4 (Comparative Examples 6 to 8) or the "extracellular vesicle solution (ultracentrifugal method, adipose-derived MSC)" obtained in Comparative Example 5 (Comparative Example 9) was used instead of the "extracellular vesicle solution (PS-affinity method)", to evaluate the anti-inflammatory action of the extracellular vesicles. The results of quantitative PCR are illustrated in FIGS. 7 to 9 together with the results of Examples 7 to 12.

It was clear from FIGS. 7 and 8 that an increase in the mRNA expression level of each of the inflammatory cytokines TNFα (FIG. 7) and IL-6 (FIG. 8) due to LPS stimulation is suppressed by the extracellular vesicles acquired by the PS-affinity method even in the case where the "extracellular vesicle solution (PS-affinity method, umbilical cord-derived MSC)" was used (Examples 7 to 10) and the case where the "extracellular vesicle solution (PS-affinity method, adipose-derived MSC)" were used, and it was found that the extracellular vesicles acquired by the PS-affinity method have the anti-inflammatory action. In addition, it was clear from FIG. 9 that a decrease in the mRNA expression level of the anti-inflammatory cytokines TGFβ1 (FIG. 9 due to LPS stimulation is suppressed by the extracellular vesicles acquired by the PS-affinity method even in the case where the "extracellular vesicle solution (PS-affinity method, umbilical cord-derived MSC)" was used (Example 11) and the case where the "extracellular vesicle solution (PS-affinity method, adipose-derived MSC)" (Example 12) were used, and it was found that the extracellular vesicles acquired by the PS-affinity method have the anti-inflammatory action.

It was found from these results that the extracellular vesicles obtained from mesenchymal stem cells by the PS-affinity method have the anti-inflammatory action regardless of the type of mesenchymal stem cells. In addition, the extracellular vesicles (Examples 7 to 12) acquired from mesenchymal stem cells by the PS-affinity method have a remarkably higher anti-inflammatory action than the extracellular vesicles (Comparative Examples 6 to 9) acquired from mesenchymal stem cells by the ultracentrifugal method, regardless of the type of mesenchymal stem cells.

According to the present invention, the anti-inflammatory agent containing the extracellular vesicles having an inflammatory cytokine production inhibitory action, which are acquired from mesenchymal stem cell-derived extracellular vesicles as an active ingredient, is provided, and the present invention has great industrial availability in that an effective therapeutic medication for chronic inflammation such as rheumatoid arthritis and ulcerative colitis caused by overproduction of inflammatory cytokines, crohn's disease, and furthermore, various diseases such as type 2 diabetes, depression, obesity, septicemia, atherosclerosis, dermatitis, dementia, general dementia, parkinson's disease, is provided based on the inflammatory cytokine production inhibitory action.

Sequence List

2156_ST250002.txt

What is claimed is:

1. A method of using a phosphatidylserine-positive extracellular vesicle for repressing inflammation, wherein the extracellular vessel is obtained from a mesenchymal stem cell-derived extracellular vesicle by a method of using a substance having an affinity for phosphatidylserine.

2. The method according to claim 1, wherein the mesenchymal stem cell is a cell derived from an induced pluripotent stem cell or a cell derived from one or more tissues selected from the group consisting of umbilical cord, umbilical cord blood, bone marrow, adipose, muscle, nerve, skin, amniotic membrane, and placenta.

3. The method according to claim 1, wherein the substance having an affinity for phosphatidylserine is a Tim protein.

4. The method according to claim 3, wherein the Tim protein is selected from Tim4 protein, Tim3 protein, and Tim1 protein.

* * * * *